(12) United States Patent
Pelerossi et al.

(10) Patent No.: US 7,699,054 B2
(45) Date of Patent: *Apr. 20, 2010

(54) POSITIVE EXPIRATORY PRESSURE DEVICE

(75) Inventors: Richard K. Pelerossi, Rome, NY (US);
Gregory S. King, Cazenovia, NY (US);
Jennifer M. Foran, Bridgeport, NY
(US); Lawrence A. Weinstein,
Chesterfield, VA (US); **Fredrick M.
Richards**, Clinton, NY (US);
Christopher T. Zirps, Sharon, MA
(US); Robert H. Elden, Cambridge, MA
(US)

(73) Assignee: Smiths Medical ASD, Inc., Keene, NH
(US)

( * ) Notice: Subject to any disclaimer, the term of this patent is extended or adjusted under 35 U.S.C. 154(b) by 321 days.

This patent is subject to a terminal disclaimer.

(21) Appl. No.: 11/311,733

(22) Filed: Dec. 19, 2005

(65) Prior Publication Data

US 2006/0090753 A1   May 4, 2006

Related U.S. Application Data

(63) Continuation of application No. 10/396,218, filed on Mar. 24, 2003, now Pat. No. 7,059,324, which is a continuation-in-part of application No. 09/449,208, filed on Nov. 24, 1999, now Pat. No. 6,581,598.

(51) Int. Cl.
*A62B 9/02* (2006.01)
*A61M 15/00* (2006.01)
*A61M 16/00* (2006.01)

(52) U.S. Cl. .............................. 128/205.24; 128/200.24

(58) Field of Classification Search ............ 128/205.24, 128/204.19, 204.23, 202.22, 205.23; 600/529, 600/533, 538, 540; 482/13

See application file for complete search history.

(56) References Cited

U.S. PATENT DOCUMENTS

| | | | | |
|---|---|---|---|---|
| 3,643,686 A | * | 2/1972 | Koegel, Ewald | 137/512 |
| 3,867,985 A | * | 2/1975 | Wilkinson | 166/329 |
| 3,908,987 A | * | 9/1975 | Boehringer | 482/13 |
| 3,949,938 A | * | 4/1976 | Goodinge | 239/102.2 |
| 4,231,375 A | * | 11/1980 | Boehringer et al. | 600/538 |
| 4,245,633 A | * | 1/1981 | Erceg | 128/205.17 |
| 4,454,893 A | * | 6/1984 | Orchard | 137/494 |
| 4,552,142 A | * | 11/1985 | Hoffman et al. | 128/207.16 |
| 4,601,465 A | * | 7/1986 | Roy | 482/13 |
| 4,611,591 A | * | 9/1986 | Inui et al. | 128/205.24 |
| RE32,553 E | * | 12/1987 | Bennett et al. | 137/271 |
| 4,828,648 A | * | 5/1989 | La Chapelle et al. | 117/58 |
| 5,020,532 A | * | 6/1991 | Mahoney et al. | 128/205.24 |
| 5,065,746 A | * | 11/1991 | Steen | 128/205.24 |
| 5,067,487 A | * | 11/1991 | Bauman | 128/205.13 |
| 5,109,840 A | * | 5/1992 | Daleiden | 128/205.13 |
| 5,193,529 A | * | 3/1993 | Labaere | 128/200.24 |
| 5,277,195 A | * | 1/1994 | Williams | 600/538 |
| 5,301,667 A | * | 4/1994 | McGrail et al. | 128/205.14 |

(Continued)

*Primary Examiner*—Steven O Douglas
*Assistant Examiner*—Annette F Dixon
(74) *Attorney, Agent, or Firm*—Luedeka, Neely & Graham, P.C.; August E. Roehrig, Jr.

(57) ABSTRACT

A multi-use, hand held, single patient oscillatory positive expiratory pressure respiratory therapy device which is easily assembled and disassembled for cleaning, and which is not position dependent during therapy, but operable through a wide range of device orientation.

6 Claims, 8 Drawing Sheets

U.S. PATENT DOCUMENTS

| | | | |
|---|---|---|---|
| 5,348,411 A * | 9/1994 | Ozu et al. | 401/219 |
| 5,357,951 A * | 10/1994 | Ratner | 128/205.24 |
| 5,421,190 A * | 6/1995 | Brandle et al. | 73/30.01 |
| 5,439,430 A * | 8/1995 | Rubens et al. | 482/13 |
| 5,451,190 A * | 9/1995 | Liardet | 482/13 |
| 5,598,839 A * | 2/1997 | Niles et al. | 128/205.23 |
| 5,899,832 A * | 5/1999 | Hougen | 482/13 |
| 6,095,139 A * | 8/2000 | Psaros | 128/204.22 |
| 6,102,038 A * | 8/2000 | DeVries | 128/205.24 |
| 6,283,122 B1 * | 9/2001 | Adahan | 128/205.24 |
| 6,581,598 B1 * | 6/2003 | Foran et al. | 128/204.23 |
| 6,776,159 B2 * | 8/2004 | Pelerossi et al. | 128/204.18 |
| 6,886,561 B2 * | 5/2005 | Bayron et al. | 128/205.24 |
| 6,910,479 B1 * | 6/2005 | Van Brunt | 128/204.18 |
| 6,997,181 B2 * | 2/2006 | Fletcher | 128/202.15 |
| 7,059,324 B2 * | 6/2006 | Pelerossi et al. | 128/204.18 |
| 7,066,174 B1 * | 6/2006 | Smith et al. | 128/205.24 |
| 7,066,177 B2 * | 6/2006 | Pittaway et al. | 128/205.24 |
| 7,096,866 B2 * | 8/2006 | Be'eri et al. | 128/205.19 |

* cited by examiner

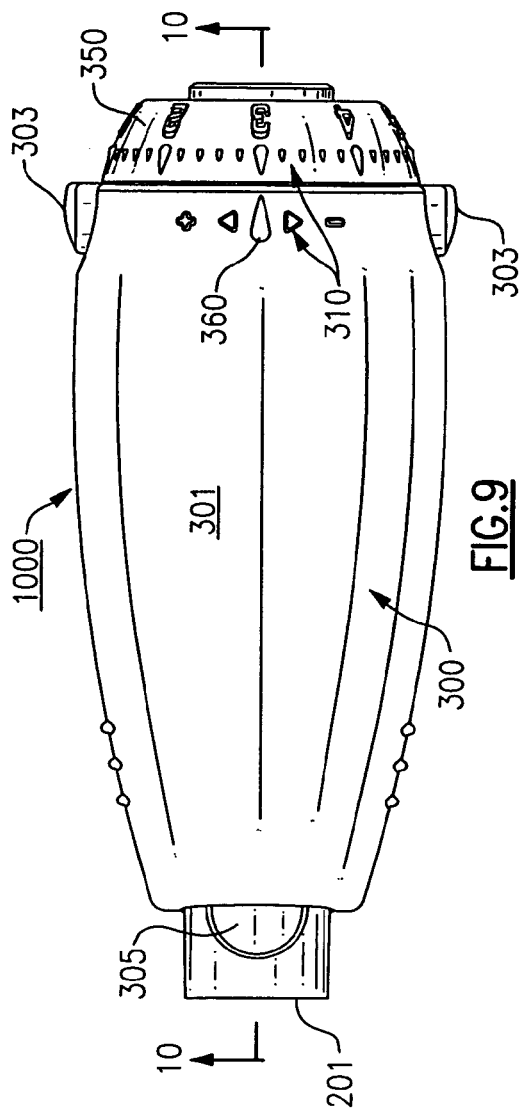
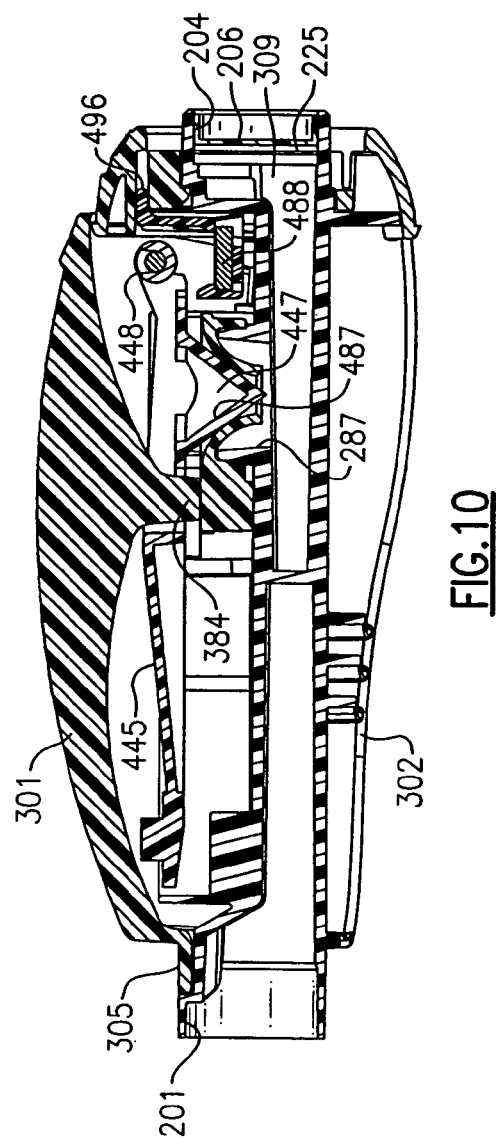
FIG. 9
FIG. 10

POSITIVE EXPIRATORY PRESSURE DEVICE

This application is a continuation of copending application Ser. No. 10/396,218 filed Mar. 24, 2003 now U.S. Pat. No. 7,059,324, which is a continuation-in-part of application Ser. No. 09/449,208 filed Nov. 24, 1999 now U.S. Pat. No. 6,581,598.

BACKGROUND OF THE INVENTION

1. Field of the Invention

This invention relates in general to a hand-held, multi-use, single patient positive oscillatory expiratory pressure respiratory therapy device and, in particular, to an easily assembled and disassembled positive oscillatory expiratory pressure respiratory therapy device which is not position dependent during therapy, but operable through a wide range of device orientation.

2. Description of Related Art

Persons who suffer from mucus-producing respiratory conditions that result in large amounts of mucus being produced in the lungs often require assistance in the removal of these secretions. If these secretions are allowed to remain in the lungs, airway obstruction occurs resulting in poor oxygenation and possible pneumonia and/or death. One of the clinically recognized treatments for this condition is a technique known as positive expiratory pressure therapy or PEP. With PEP therapy, a patient exhales against a resistance to generate expiratory pressure at a substantially constant rate of flow. Prescribed expiratory pressures are generally in the range of 10-20 cm of $H_2O$, although other pressure ranges and pressures can be used, with a preferred flow rate of between 10-25 liters per minute.

In the use of PEP therapy, a patient breaths through an orifice restricter to generate a positive pressure in the lungs during exhalation, with the pressure falling to zero at the end of the exhalation. By selection of the proper-sized orifice, a given pressure is determined for the exhalation flow rate generated by an individual patient. This extended, substantially constant, flow of elevated-pressure exhalation has been shown to be effective for moving secretions trapped in the lungs to the larger airways where the secretions can then be removed through coughing. It has also been found that in the treatment of patients having chronic obstructive pulmonary disease (COPD), chronic bronchitis, cystic fibrosis, atelectasis, or other conditions producing retained secretions, treatment with PEP therapy is improved by combining positive expiratory pressure therapy with airway oscillation and intermittent air-flow acceleration. To this end a hand-held, single patient multi-use, positive expiratory pressure respiratory therapy device was developed by assignees of the present invention, and is the subject matter of a co-pending application, Ser. No. 09/449,208, filed Nov. 24, 1999 for "POSITIVE EXPIRATORY PRESSURE DEVICE".

The present invention comprises a positive oscillatory expiratory pressure respiratory therapy device which is easily assembled and disassembled for the purpose of cleaning, and is not position dependent for operation during PEP therapy. In addition, the translucency of the device housing permits inspection of the interior to insure that condensate is not being retained in the device, and the device construction is such that any condensate forming in the device may be easily removed.

SUMMARY OF THE INVENTION

The present invention is directed to overcoming one or more of the problems or disadvantages associated with the relevant technology. As will be more readily understood and fully appreciated from the following detailed descriptions of preferred embodiments, the present invention is embodied in a positive oscillatory expiratory air pressure respiratory therapy device which is easily assembled and disassembled for cleaning and not position dependent for operation.

DESCRIPTION OF THE DRAWINGS

Further objectives of the invention, together with additional features contributing thereto and advantages accruing therefrom, will be apparent from the following description of preferred embodiments of the invention which are shown in the accompanying drawings with like reference numerals indicating corresponding parts throughout, wherein:

FIG. 9 is a top elevation view of the assembled device;

FIG. 10 is a sectional view of the device as illustrated in FIG. 9 taken along lines 10-10 to better illustrate the internal structure for creating the oscillatory positive expiratory air pressure and to control the oscillatory frequency and pressure, and the manner in which the magnitude and frequency of the oscillations can be adjusted;

DETAILED DESCRIPTION OF THE INVENTION

Figure 1:
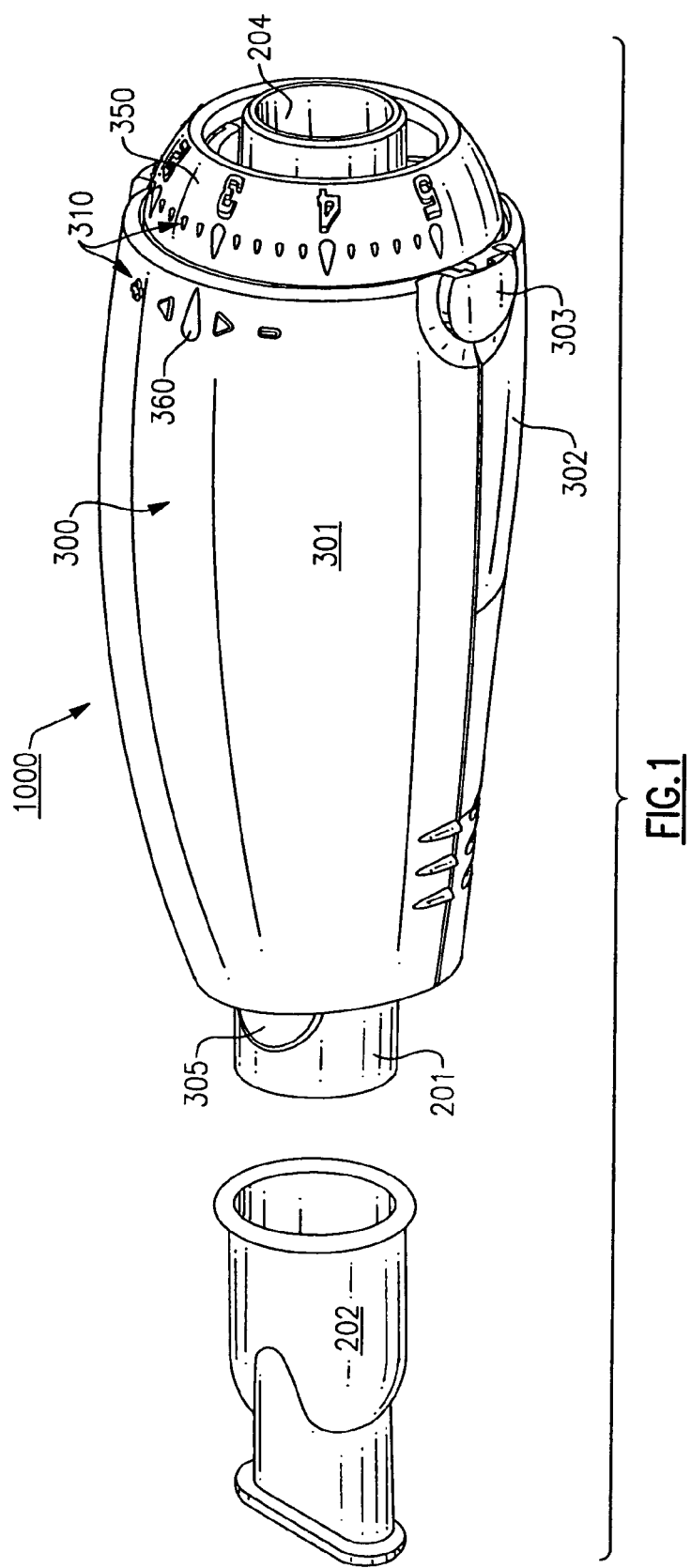
FIG. 1 is a perspective view of a first embodiment of the assembled invention.
Figure 2:
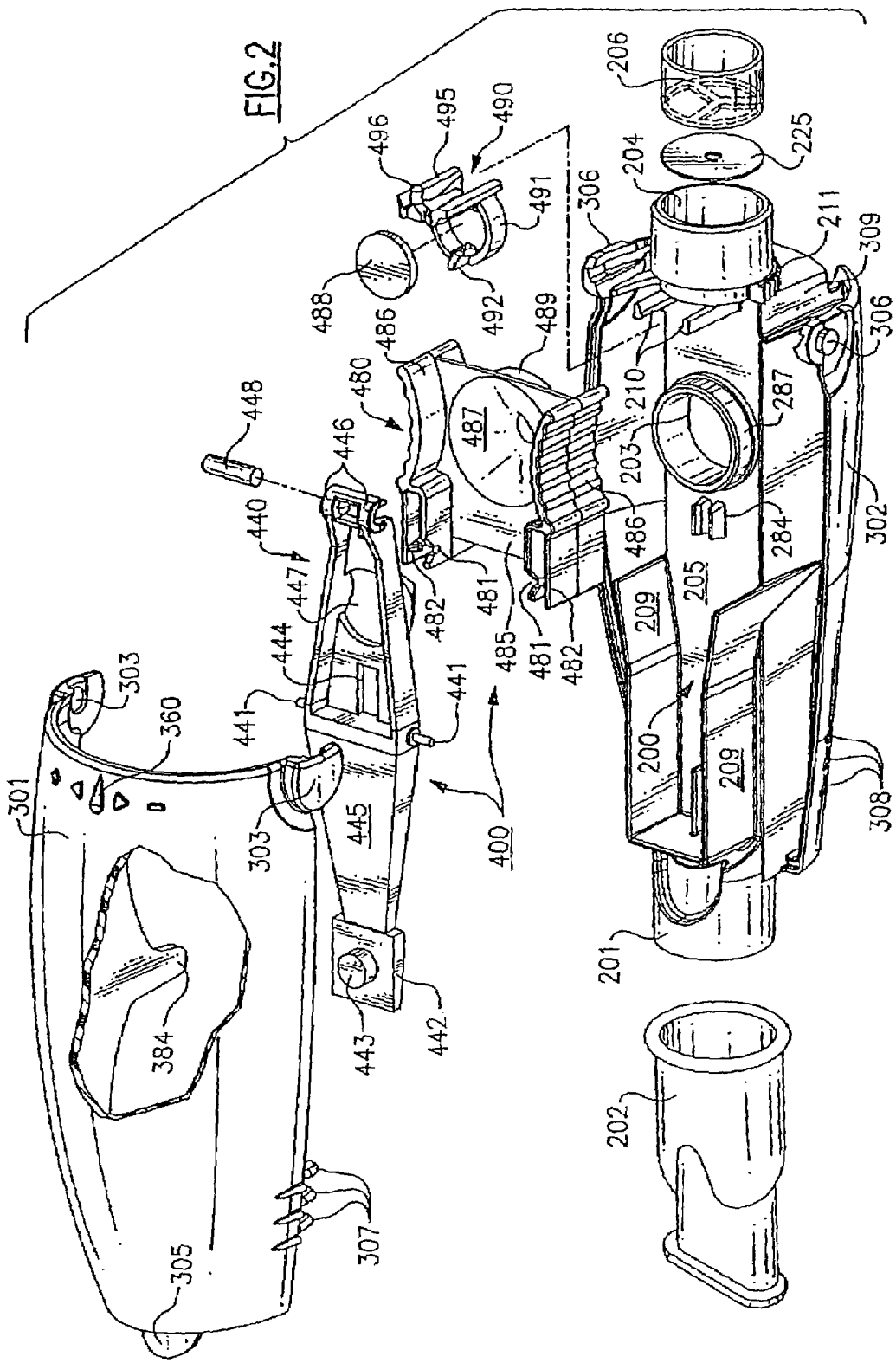
FIG. 2 is an exploded perspective view of the invention illustrated in FIG. 1 with portions removed to better illustrate the internal structure thereof.
Figure 3:
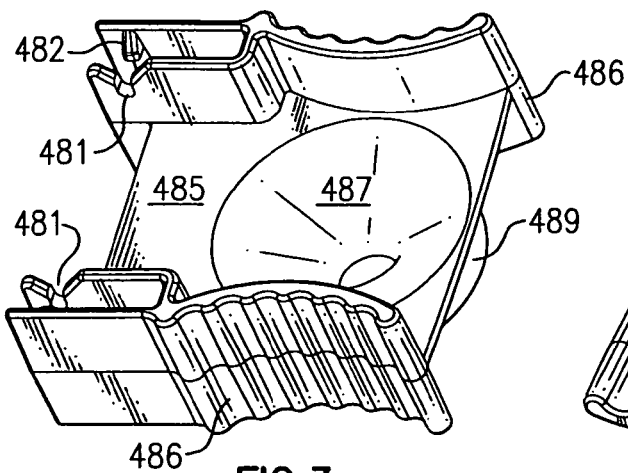
FIGS. 3, 4, 5 and 6 are, respectively, an upper and lower perspective view, top elevation and sectional view of the platform portion of the invention to better illustrate a portion of the structure forming the non-linear orifice.

Referring now to the drawings, there is illustrated in FIGS. 1 and 2 an oscillatory positive expiratory pressure (PEP) respiratory therapy device 1000 for applying oscillatory positive expiratory air pressure (PEP) therapy to a patient. When expiratory air is passed from a patient through an air-flow tube 200 to an expiratory-air-driven oscillatory rocker assembly 400 contained within a two-part housing 300, the expiratory-air-driven oscillatory rocker assembly 400 creates an oscillatory positive expiratory air pressure which is applied to the patient during exhalation. The expiratory-air-driven oscillatory rocker assembly 400 comprises two portions, a rocker portion 440 and a rocker support or platform portion 480 which act together in creating the oscillatory PEP therapy and are best illustrated in FIGS. 2-10. The details of the structure and operation of this oscillatory PEP portion of the device will be described in detail hereinafter.

To control the magnitude and frequency of the oscillatory pressure applied to a patient, a rotatable frequency control dial 350 is carried by and positioned at the discharge end of an air-flow tube 200. The air-flow tube 200 is carried by a lower housing portion 302, and supports the rocker assembly 400. By operation of the adjustable frequency control dial 350 in a manner to be hereinafter described, the relative positioning between the oscillatory PEP inducing portions of the oscillatory rocker assembly 400, the rocker portion 440 and the rocker support portion 480, is adjusted to control the magnitude and frequency of the oscillatory expiratory air pressure.

The expiratory-air-driven oscillatory rocker portion 440 is best illustrated in the exploded view of FIG. 2, and FIGS. 7, 8 and 10. The rocker support portion 480, which functions in cooperation with the rocker portion 440 to produce an oscillatory expiratory air flow and pressure, is also illustrated in the exploded view of FIG. 2, and in more detail in FIGS. 3 through 6 and 10. The expiratory-air-driven oscillatory rocker portion 440 and the rocker support portion 480, when assembled together, form the rocker assembly 400.

The rocker assembly 400 is supported on the air-flow tube 200 which comprises a sealed chamber from a patient input end 201 to a discharge opening 203 which is periodically closed to create the oscillatory PEP treatment. In this manner, the rocker assembly 400 functions to create an oscillatory positive expiratory air pressure and flow rate in response to a patient's exhalation, and the patient's expiratory air is thereby directed to and through the rocker assembly 400.

Figure 7:
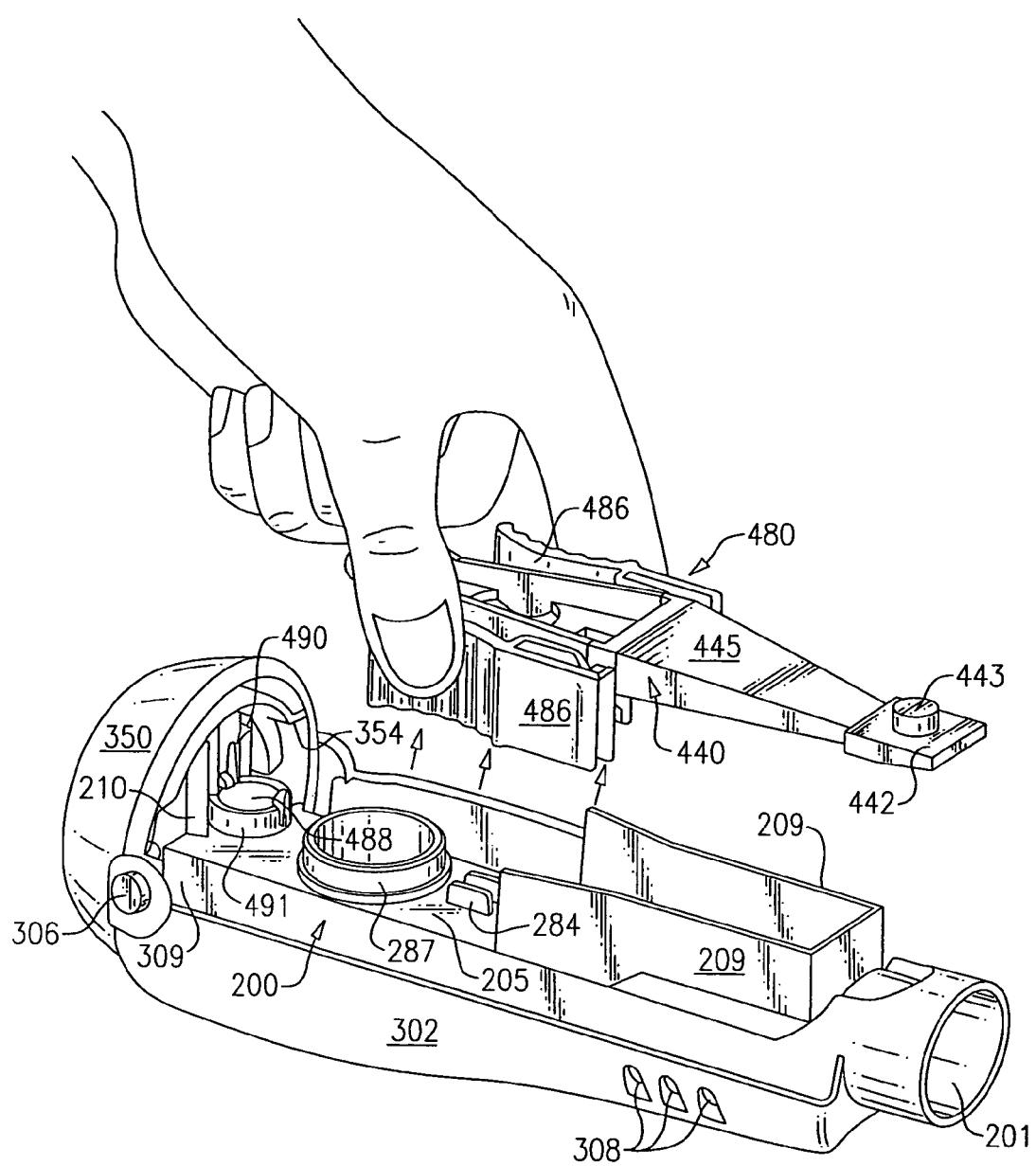
FIG. 7 is a perspective view of the rocker and platform portions of the invention as they are installed onto the lower portion of the device housing for producing an oscillatory positive expiratory air pressure.

As best shown in FIGS. 2, 7 and 10, there is illustrated the air-flow tube 200 having a first or patient input end 201 for receiving a standard 22 mm mouthpiece 202 into which a patient discharges expiratory air. The air passed into the air-flow tube through the input 201 passes out of the air-flow tube 200 through a discharge opening 203, and is applied to the rocker assembly 400. The air-flow tube discharge opening 203 is formed in the top flat planar surface 205 of the air-flow tube 200 and the expiratory air passed there through is applied to the oscillatory rocker assembly 400 for creating the oscillatory PEP therapy for the patient in a manner to be hereinafter described in detail.

While a second opposite end of the air-flow tube could be closed, for convenience of use, the opposite end 204 is open and carries a conventional one-way flapper valve 225. The flapper valve 225 allows a patient to draw inspiratory air into the air-flow tube 200 through the opening 204, but prevents expiratory air from being passed out of the air-flow tube 200 through the opening 204. To this end the one-way flapper valve 225 is positioned on a spider 206 which is inserted into the opening 204 against a shoulder forming a space sufficient for the one-way operation of the valve. Upon inhalation by a user, the valve 225 opens and allows air to pass into the air-flow tube 200, and upon exhalation, the valve 225 is held closed against the spider 206 thereby preventing expiratory air from passing out through the valve 225. If the end 204 were closed, a user would not be able to inhale through the device 1000, but that would not effect the operation of the device in providing oscillatory PEP therapy in the manner to be described herein.

After the expiratory air is applied to the rocker assembly 400, the air thereafter exits from the device 1000 through openings in the rotatable adjusting dial 350 carried in the housing 300.

As best illustrated in FIGS. 2, 7, 8 and 10, the rocker portion 440 is balanced for pivotal movement about pivot pins 441 on spaced pivot supports 481 formed on a platform 485 of the rocker support portion 480. The pivot pins 441 form a transverse pivot axis for the rocker portion 440 which lies in a plane above and extends transverse to the longitudinal axis of the platform 485. The pivot pins 441 are limited in their axial and vertical movement by a pair of locking guides 482, carried by the platform 485, one of which is positioned adjacent each of the pivot supports 481 to maintain the pivot pins 441 in their proper position on the pivot supports 481. In this manner the rocker portion 440 is pivotal relative to the rocker support portion 480 regardless of the orientation of the device 1000, allowing the oscillatory PEP device 1000 to function regardless of its orientation in use. A balance pad 442 and balancing cylinder 443 are formed at one end of a rocker arm 445 to balance the weight of a cone-shaped air-flow closure member 447 and a pin of magnetically attractable material, such as a steel pin 448, both of which are carried at the opposite end of the rocker arm 445. The pin 448 is carried at the distal end of the rocker arm 445 by a plurality of gripping fingers 446 which partially encircle the pin 448 for holding the pin in a position to be exposed to the magnetic field of a disc-shaped magnet 488 carried on the air-flow tube 200 in a magnet holder 490.

The cone-shaped air-flow closure member or air-flow closure cone 447 is sized and positioned on the rocker arm 445 to be periodically inserted into a tapered bell-shaped or trumpet-shaped air-discharge outlet 487 formed in the platform 485 to create the oscillatory PEP when expiratory air is discharged through the opening 203 in the air-flow tube 200. As best illustrated in FIGS. 3-6, the interior of the air-discharge outlet 487 has a non-linear taper or bell-shaped interior surface to form a non-linear air discharge outlet for creating the oscillatory PEP therapy in response to the pivotal movement of the air-flow closure cone 447 in to and out therefrom. In this manner the discharge outlet 487 is periodically closed and re-opened allowing the expiratory air discharged there through to be discharged from the housing 300 through the openings in the adjusting dial 350.

Figure 4:
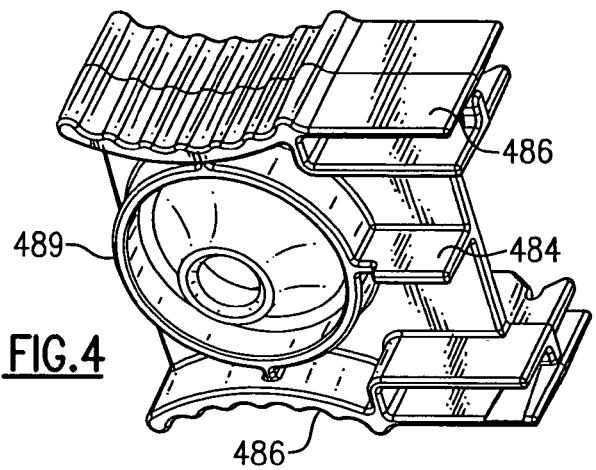
Figure 5:
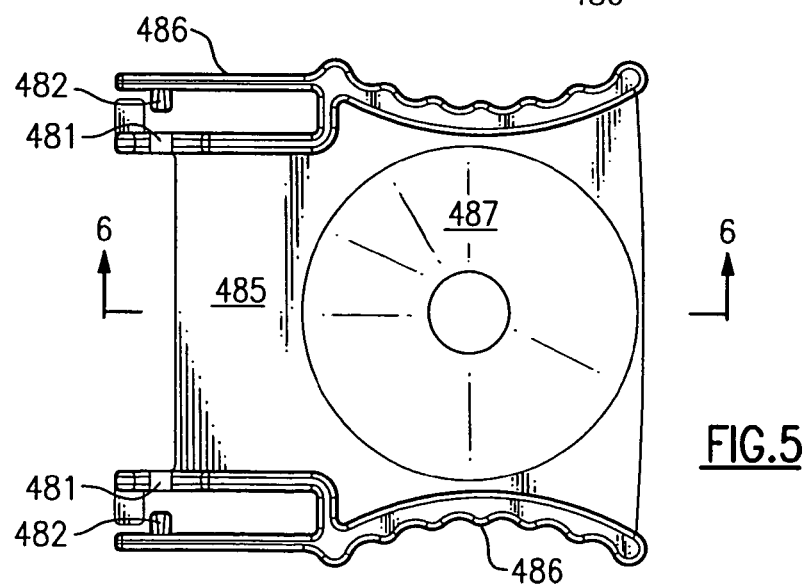
Figure 6:
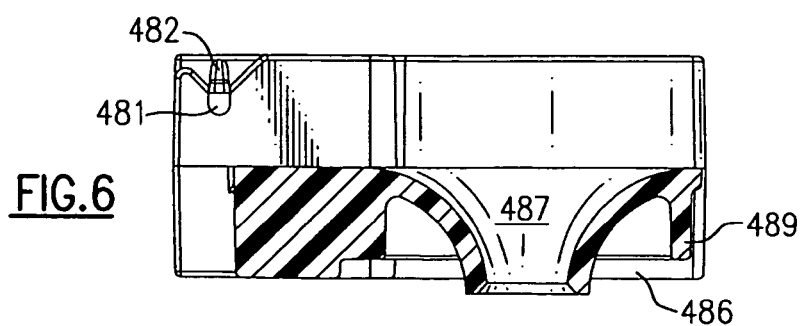

The oscillatory rocker assembly 400 is secured on the air-flow tube 200 and positioned within the housing 300 by means of a positioning tang 484 which extends downwardly from the platform 485 as best illustrated in FIGS. 2, 4 and 6. A pair of side walls 486 of the platform 485, the bottoms of which rest on the planar surface of the air-flow tube 200, are formed with a ridged finger-engaging surface to facilitate the removal and repositioning of the rocker support portion 480 relative to the air-flow tube 200 for cleaning the device 1000 as necessary. Sidewalls 209 extend vertically outward from the planar surface 205 of the air-flow tube 200 and are spaced apart a distance sufficient to receive the rocker arm 445 there between. In this manner, the rocker arm is protected between the sidewalls 209 when the upper and lower housing portions, 301 and 302, respectively are separated for cleaning. This positioning protects the rocker assembly 400 from being inadvertently improperly grasped by a user when disassembling the device 1000 for cleaning, and the user's attention is directed to the ribbed or ridged finger-engaging surface of the side walls 486 which are preferred for grasping when the rocker assembly is to be removed.

The tang 484 is secured in a channel 284 extending upwardly from the top of the planar surface 205 of the air-flow tube 200 to securely position the oscillatory rocker assembly 400 onto the air-flow tube 200. In this manner a circular guide 489 engages with a cowling 287 of the complementary airflow tube discharge opening 203 so that the non-linear tapered, bell-shaped discharge outlet 487 carried by the platform 485 is aligned in fluid communication with and extends into the discharge opening 203 in the air-flow tube 200. Another tang 384 extends downwardly from the interior of upper portion 301 of the housing 300 and passes through an aperture 444 in the rocker arm 445 to press downwardly against the platform 485 thereby securing the oscillatory rocker assembly 400 in the proper position on the air-flow tube 200 when the upper 301 and lower 302 portions of the housing 300 are engaged.

Figure 8:
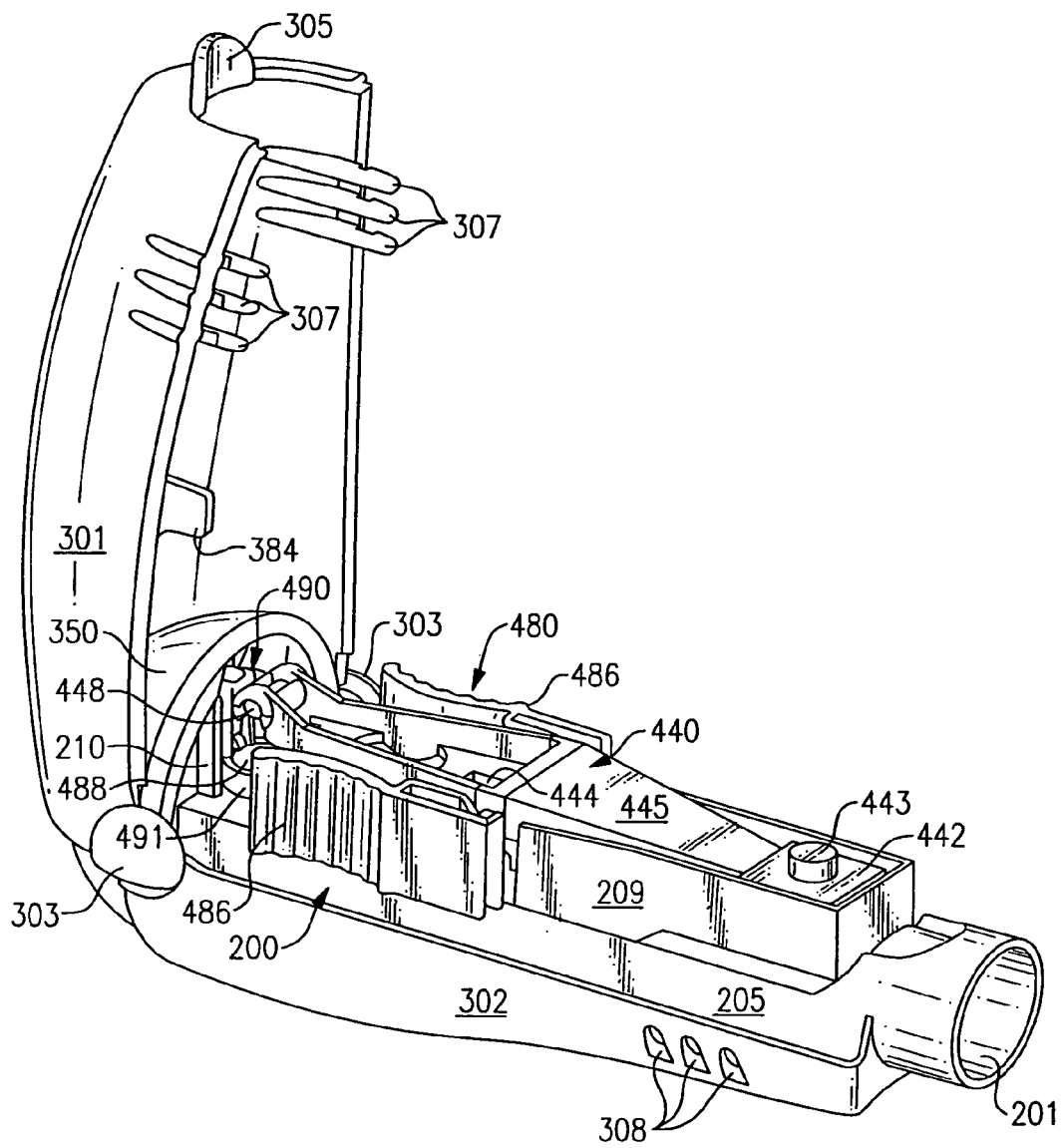
FIG. 8 is a perspective view of the assembled device with the upper portion of the device open to better illustrate a portion of the structure for adjusting the magnitude and frequency of the oscillatory positive expiratory air pressure and the ease in which the device may be assembled and disassembled for cleaning.

The upper and lower portions of the housing, 301 and 302, respectively, are pivotally connected to facilitate the opening and closing of the housing such as when it is desired to clean the interior thereof. To this end, as best illustrated in FIGS. 2 and 8, the upper housing 301 is formed with a pair of tabs 303 for engaging a pair of complementary pivot pins 306 formed on the lower housing 302 in a position to engage the tabs 303 to form a pivotal connection therewith. A plurality of pins 307 extend outwardly from the upper housing 301 to engage complementary receptacles 308 formed on the lower housing 302 to maintain the two portions of the housing closed unless it is desired that they be opened for access to the interior of the housing 300. When it is desired to open the housing 300, the sides of the upper housing portion 301 are compressed towards each other to facilitate releasing the pins 307 from the receptacles 308. When the pins 307 are so positioned, the two housing portions 301 and 302 are enabled to be pivoted relative to each other about the pivot connection 303, 306 providing access to the interior of the housing 300 and the components enclosed therein. A securing tab 305 extends outwardly from the end of the upper housing 301 opposite to the tabs 303 to engage a complementary recess formed in the lower housing 302 to facilitate securing the two housing portions 301, 302 of the housing 300 together and the mouthpiece 202 is passed over the tab 305 when place onto the end 201 of the air-flow tube 200.

To create the periodically interrupted discharge of expiratory air for applying the oscillatory PEP therapy to a patient, the magnetically attractable material or steel pin 448 is carried on the pivotal rocker arm 445 at a position in operative proximity to the magnet 488 carried by the rocker support portion 480. While the rocker assembly 400 may be constructed without magnetically attractable material and a magnet/magnet holder, the device 1000 will still provide oscillatory PEP therapy. The use of the magnetic material and magnet/magnet holder permits the device 1000 to control the magnitude and frequency of the oscillations.

Figure 11:
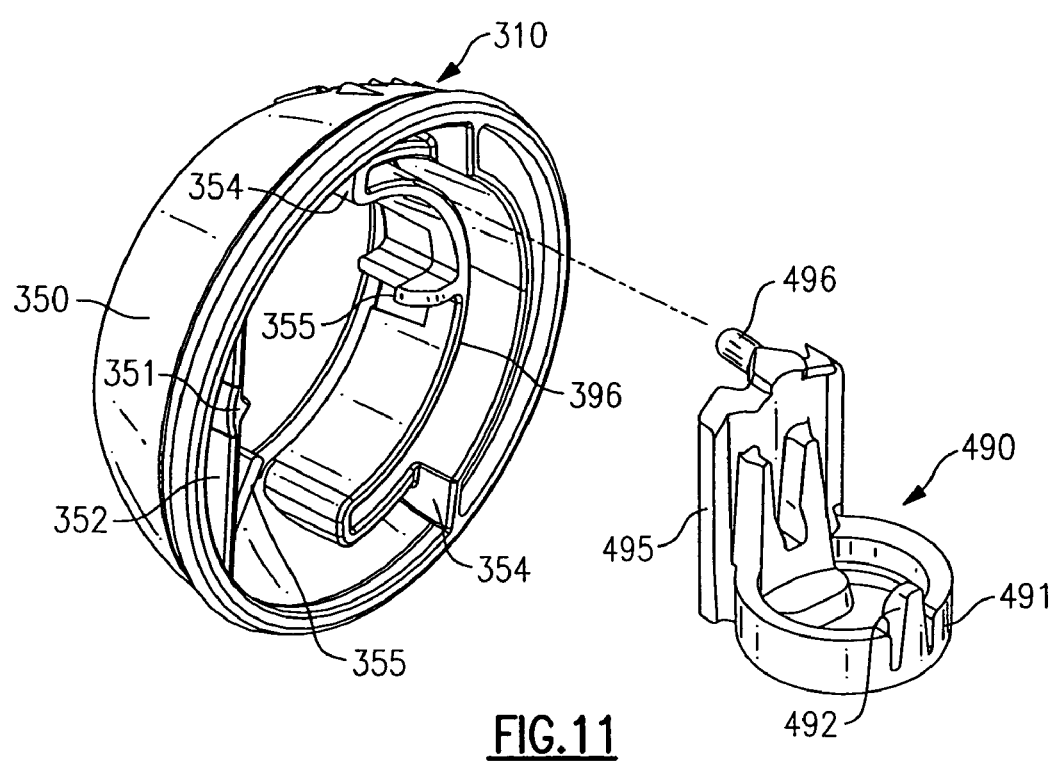
FIG. 11 is a rear perspective view of an adjustment dial portion of the invention to better illustrate the manner in which the platform portion illustrated in FIGS. 3-6 is positionable relative to the rocker portion illustrated in FIG. 2 to determine the magnitude and frequency of the oscillations.

The magnet 488 is carried in a magnet holder 490 having a receiver portion or pocket 491 formed in a circular configuration for receiving the disc-shaped magnet 488, and has a plurality of gripping or centering fingers 492 for retaining the magnet 488 in the circular-shaped receiver pocket. The receiver pocket 491 is formed at one end of a vertically positionable carrier 495, which is guided in its vertical movement by a pair of guide rails 210 extending outwardly from the flat planar surface 205 of the air-flow tube 200. The opposite end of the carrier 495 extends vertically upward from a position adjacent to the circular-shaped receiver pocket 491 and terminates in a follower tip 496 which engages a cam surface 396 formed in the oscillation frequency control dial 350, as illustrated in FIGS. 7, 8 and 11.

In this manner, rotation of the frequency control dial 350 will move the follower tip 496 causing the carrier 495 to move vertically between the guide rails 210. Raising or lowering the carrier 495 moves the magnet 488 towards or away from the steel pin 448 to vary the magnetic attractive force there between. Rotation of the frequency control dial 350 controls the frequency of the oscillations by which the PEP treatment or therapy is applied in accordance with the desires of the healthcare provider. While the device 1000 will function to provide an oscillatory PEP pulse without the use of the magnetic field between the magnet 488 and the steel pin 448, because of the opening and closing of the tapered non-linear discharge outlet 487 due to the movement of the tapered cone-shaped air-flow closure 447 induced in response to the patient's discharge of expiratory air, the use of the magnetic field permits the device 1000 to provide an adjustable range in the pressure of the patient's expiratory air discharge required to create the oscillatory positive expiratory pressure pulses.

Figure 12:
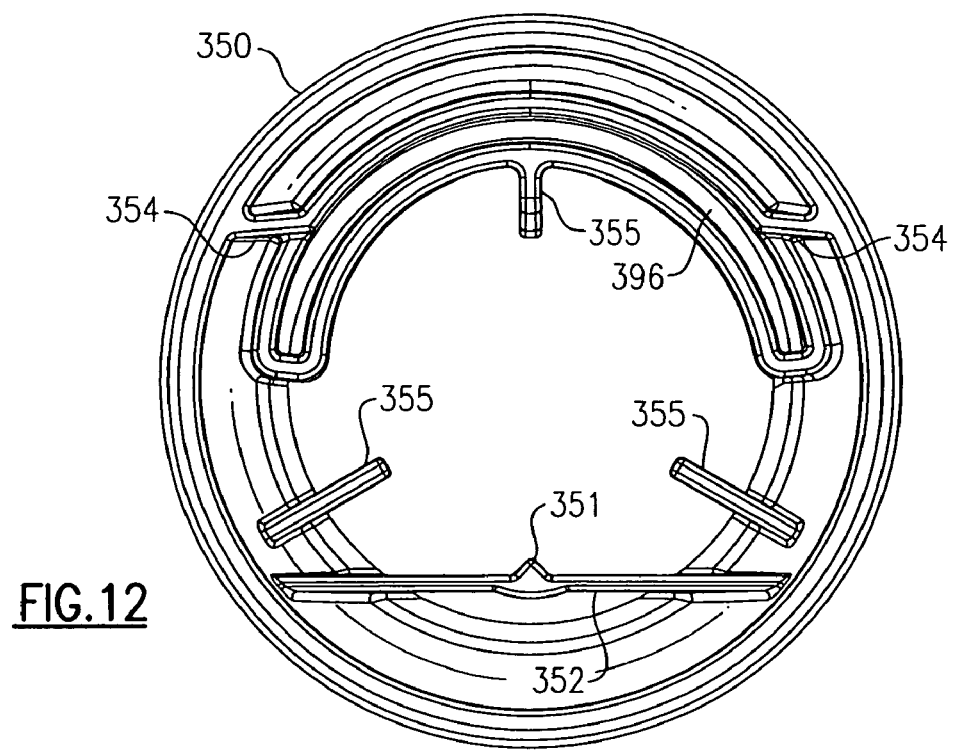
FIG. 12 is a planar view of the adjustment dial illustrated in FIG. 11 to better illustrate the structure and function thereof.

To assist a patient or the healthcare provider in using the device 1000 once the proper magnetic field has been set, a plurality of indicia 310 are spaced along the control dial 350 and the top of the upper portion 301 of the housing 300. These indicia 310, in combination with a base reference point 360 on the upper housing 301, are used to ensure that the correct setting is being maintained after the healthcare provider has established the desired level for treatment. To minimize the occurrence of the rotatable adjusting dial 350 being unknowingly rotated, as best illustrated in FIG. 2 a series of tooth-like projections 211 are formed on the air-flow tube 200. These projections are engaged by a mating tooth 351 formed on a thin chord 352 of plastic material from which the adjusting dial 350 is constructed, and which extends across the lower internal portion of the adjusting dial to form a sounding board. In this manner, when the rotatable adjusting dial 350 is turned, the tooth-like projections 211 and the mating tooth 351 provide resistance to movement and produce a mechanically generated audible sound to signal that a change in position has occurred. A pair of stops 354 are formed on the interior of the adjusting dial 350, best illustrated in FIGS. 11 and 12, which in combination with a side portion 309 of the lower housing 302, limit the rotational movement of the dial 350 relative to the housing 300.

The rotatable adjusting dial 350 is rotatably mounted on the end of the air-flow tube 200 adjacent to the end 204 thereof, and is held in contact by a snap fit therewith and guides 355 which provide three point contact between the dial 350 and the end of the air-flow tube. As expiratory air is passed through the rocker assembly 400 the air will freely flow from the housing 300 through the spaces between the housing 300 and the adjusting dial 350.

Figure 13:
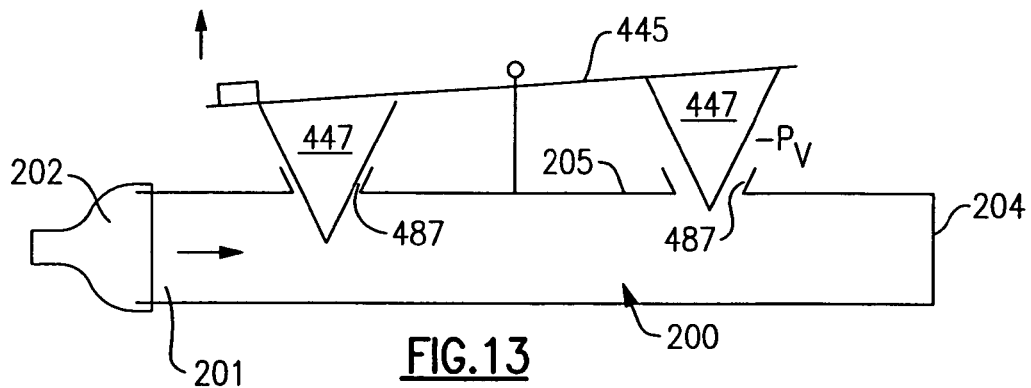
FIG. 13 is a mechanical schematic of a second embodiment of the invention utilizing dual rocker and platform assemblies to generate an oscillatory positive expiratory air pressure.
Figure 14:
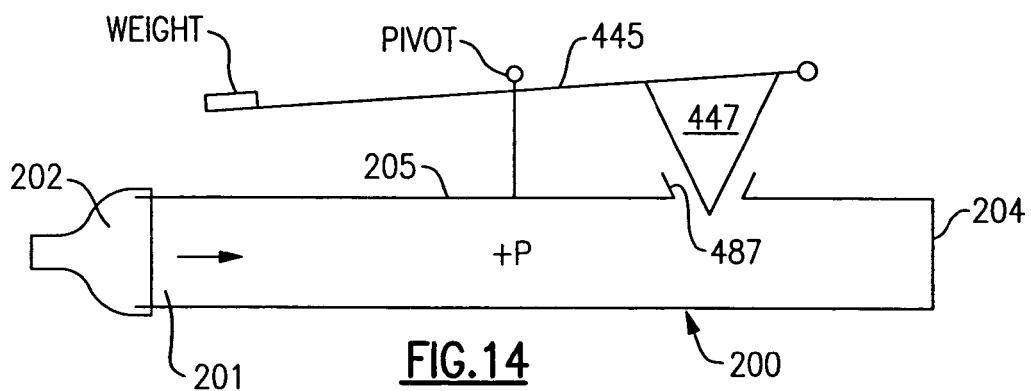
FIG. 14 is a mechanical schematic of a third embodiment of the invention utilizing the platform and rocker assembly as illustrated herein, but without a magnet control to generate an oscillatory positive expiratory air pressure.

Referring now to the embodiments illustrated in FIGS. 13 and 14, there are illustrated two additional embodiments of the invention utilizing a rocker assembly 400 carried on an air-flow tube 200. In the embodiment illustrated in FIG. 13, two cone-shaped air-flow closure members or air-flow closure cones 447 are utilized supported, one at each end, on a rocker arm 445a pivotally mounted at the approximate center thereof for mutually exclusively closing and opening one of a pair of complementary tapered bell-shaped or trumpet-shaped air-discharge outlets 487 formed in the air-flow tube 200 carried within a housing 300, not shown in this illustration. As shown in this Fig. the end 204 of the air-flow tube is closed, but could be formed with a one-way valve 225 as previously described. In this embodiment it is believed that the flow of air out of one of the air-discharge outlets 487 will cause the complementary air-flow closure cone 447 to be accelerated downwardly increasing the pressure in the air-flow tube such that the other air-flow closure cone 447 will be forced upwardly from its associated air-discharge outlet 487 until the flow of expiratory air through the outlet 487 and over the combination of the conical surface of the air-flow closure cone 487 and the tapered non-linear orifice of the air-discharge outlet 487 will cause the cone 447 to be accelerated downwardly towards the outlet 487 repeating the cycle and generating an oscillatory expiratory air pulse to the user as the two discharge outlets are cycled on and off.

The embodiment illustrated in FIG. 14 is similar to the embodiment described herein without the magnetic 488 and magnet carrier 495. In this embodiment there would be no oscillatory frequency control and, therefore, no need for a frequency adjusting dial 350. The unit would not be operable in all orientations, but would still provide oscillatory PEP therapy at a fixed frequency which would be dependent upon the weight of the rocker assembly components.

Figure 15:
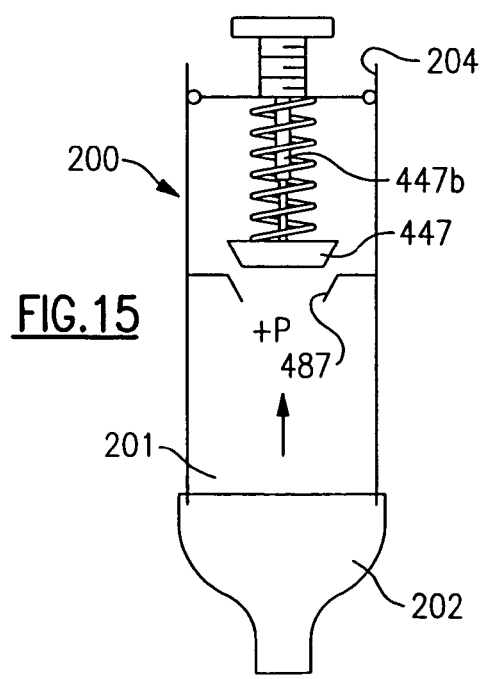
FIG. 15 is a mechanical schematic of a fourth embodiment of the invention utilizing a spring-biased air-flow closure to generate an oscillatory positive expiratory air pressure.

In the embodiment illustrated in FIG. 15, the air-flow tube 200 has an open end 204 through which expiratory air passes after passing through a modified air-flow closure cone 447 and associated air-discharge outlet 487. The air-flow closure cone 447 is mounted on a spring-loaded shaft 447b which is adjustable to vary the force which is applied to hold the air-flow closure cone 447 against the expiratory air pressure applied through the associated air-discharge outlet 487. When the expiratory air pressure increases above the spring force applied to the air-flow closure cone 447, the expiratory air will be discharged through the associated air-discharge outlet functioning in the manner here to fore described and causing an oscillatory PEP to be applied to the user.

INDUSTRIAL APPLICABILITY

During use of the variable frequency or oscillatory PEP device 1000 a patient's expiratory air is delivered through the input end 201 of the air-flow tube 200 and passes through the opening 203 to the oscillatory rocker assembly 400. Accordingly, the expiratory air pressure is applied against the cone-shaped closure 447 of the rocker assembly 400 which forms a closure of the non-linear discharge opening or orifice 487. The pressure of the patient's expiratory air will raise the cone-shaped closure 447, causing the rocker portion 440 to pivot about the pivot pins 441 against the force of the magnetic field between the magnet 488 carried on the pivotal rocker support portion 480 and the steel pin 448 carried on the rocker assembly 400. As the cone-shaped closure 447 moves upwardly in response to the increasing expiratory air pressure, the constant taper of the conical shape in conjunction with the bell-shaped non-linear taper of the non-linear discharge opening or orifice 487 increases the effective discharge area thereby decreasing the air pressure applied against the cone-shaped closure 447 and reducing the upward acceleration of the rocker arm 445.

When the magnetic force and the Coanda effect of the air flow over the bell-shaped or non-linear tapered interior of the discharge outlet 487 overcome the expiratory air pressure applied to the tapered cone-shaped closure 447, the closure 447 will again begin to move downwardly and accelerate into the bell-shaped non-linear-tapered discharge orifice 487. As the cone descends into the air flow path through the discharge outlet or orifice 487, the annular flow area diminishes reducing the airflow rate and increasing the air pressure. This continues until the downward momentum is overcome and the cone 447 resumes its upward acceleration. Maximum pressure is obtained at this point and another cycle begins.

While this invention has been described in the specification and illustrated in the drawings with reference to preferred embodiments, the structures of which have been disclosed herein, it will be understood by those skilled in the art to which this invention pertains that various changes may be made and equivalents may be substituted for elements of the invention without departing from the scope of the claims. Therefore, it is intended that the invention not be limited to the particular embodiments disclosed in the specification and shown in the drawings as the best modes presently known by the inventors for carrying out this invention nor confined to the details set forth, but that the invention will include all embodiments modifications and changes as may come within the scope of the following claims:

What is claimed is:

1. An oscillatory positive expiratory pressure therapy device, comprising:
    an air-flow tube having a path of air flow movement from an inlet opening for receiving expiratory air passed thereto by a user receiving respiratory therapy or care, through an outlet opening for discharging the expiratory air passed through said inlet opening;
    said air-flow tube including expiratory air responsive closure means positioned in said path of air flow movement and actuable between an open position and a closed position in response to the pressure of expiratory air passed thereto;
    said expiratory air responsive closure means including a normally closed non-linear discharge outlet which is opened in response to the presence of a predetermined pressure of expiratory air being passed in said path of air flow movement, and which closes in response to a predetermined rate of air pressure decrease through said non-linear discharge opening; and
    wherein said expiratory air responsive closure means positioned in said path of air flow movement and actuable between an open position and a closed position in response to the pressure of expiratory air passed thereto comprises an oscillatory rocker assembly including a rocker portion having a cone-shaped air-flow closure member pivotally supported on a rocker support portion to engage a tapered bell-shaped air-discharge outlet to form said non-linear air discharge outlet.

2. The oscillatory positive expiratory pressure therapy device of claim 1 wherein said non-linear discharge outlet positioned in said path of air flow movement comprises a non-linear tapered discharge orifice.

3. The oscillatory positive expiratory pressure therapy device of claim 1 wherein said non-linear discharge outlet positioned in said path of air flow movement comprises a bell-shaped discharge orifice.

4. The oscillatory positive expiratory pressure therapy device of claim 1 wherein said non-linear discharge outlet positioned in said path of air flow movement comprises a trumpet-shaped air discharge outlet.

5. The oscillatory positive expiratory pressure therapy device of claim 1 further including a magnetic force field applying means for generating a biasing force effecting the opening and closing of said non-linear discharge opening.

6. An oscillatory positive expiratory pressure therapy device, comprising:
    an air-flow tube having a path of air flow movement from an inlet opening for receiving expiratory air passed thereto by a user receiving respiratory therapy or care, through an outlet opening for discharging the expiratory air passed through said inlet opening;

said air-flow tube including expiratory air responsive closure means positioned in said path of air flow movement and actuable between an open position and a closed position in response to the pressure of expiratory air passed thereto;

said expiratory air responsive closure means including a normally closed tapered trumpet-shaped air-flow discharge outlet which is opened in response to the presence of a predetermined pressure of expiratory air being passed in said path of air flow movement, and which closes in response to a predetermined rate of air pressure decrease through said discharge opening; and said expiratory air responsive closure means including a cone-shaped air-flow closure member pivotally movable in response to expiratory air pressure between a closed position into engagement with said tapered trumpet-shaped air-flow discharge outlet blocking the flow of expiratory air in said path of air flow movement and an open position permitting the flow of expiratory air in said path of air flow movement thereby forming a non-linear discharge outlet.

* * * * *